(12) United States Patent
Melton, Jr. et al.

(10) Patent No.: US 6,717,598 B1
(45) Date of Patent: Apr. 6, 2004

(54) MEDICAL NAVIGATOR AND SYSTEMS THEREFOR

(75) Inventors: Hewlett E. Melton, Jr., Sunnyvale, CA (US); John McIntyre Douglass, Newbury Port, MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/568,555

(22) Filed: May 9, 2000

(51) Int. Cl.$^7$ ................................................ G06F 3/00
(52) U.S. Cl. ...................... 345/846; 345/835; 345/839; 368/10; 340/309.15; 700/236
(58) Field of Search ........................ 345/764, 727, 345/835, 839, 846, 978; 434/98; 368/10; 705/2, 3; 600/300, 301; 700/90, 213, 236, 231, 240; 340/309.15; 128/920

(56) References Cited

U.S. PATENT DOCUMENTS

| | | | | |
|---|---|---|---|---|
| 4,926,572 A | * | 5/1990 | Holmes | 40/448 |
| 5,347,453 A | * | 9/1994 | Maestre | 705/2 |
| 5,549,117 A | * | 8/1996 | Tacklind et al. | 600/529 |
| 5,553,609 A | * | 9/1996 | Chen et al. | 600/301 |
| 5,691,932 A | * | 11/1997 | Reiner et al. | 368/10 |
| 5,758,096 A | * | 5/1998 | Barsky et al. | 705/3 |
| 5,872,505 A | * | 2/1999 | Wicks et al. | 340/7.3 |
| 5,925,021 A | * | 7/1999 | Castellano et al. | 604/207 |
| 5,961,446 A | * | 10/1999 | Beller et al. | 600/300 |
| 6,075,755 A | * | 6/2000 | Zarchan | 368/10 |
| 6,168,563 B1 | * | 1/2001 | Brown | 600/301 |
| 6,294,999 B1 | * | 9/2001 | Yarin et al. | 340/573.1 |
| 6,335,907 B1 | * | 1/2002 | Momich et al. | 368/10 |
| 6,421,650 B1 | * | 7/2002 | Goetz et al. | 705/3 |

FOREIGN PATENT DOCUMENTS

WO WO 94/04966 A1 * 3/1994 ........... G04B/47/00
WO WO 01/74229 A2 * 10/2001

OTHER PUBLICATIONS

Michael Goodwin, "Take Two Aspirins, Call Your PC in the Morning," Jun. 1994, PC World, pp. 315–318.*
Saty Satya–Murti, "Clinical Pharmacology," Nov. 23–30, 1994, JAMA, vol. 272, No. 20, pp. 1628–1629.*
Leigh Anne Brown, "Improving medication compliance: A key to good mental health," Sep. 7, 1996, Drug Topics, v142, n17, p38(1).*
"Open Text: Open Text search technology to power PDR Electronic Library on CD–ROM," M2 Presswire, Oct. 23, 1996.*
Somerville KT et al, "An Internet–Based Patient Education Tool Utilising Medication Pictures To Overcome Barriers To Learning About Complex Transplant Medication Regimes," Mar. 2000, Pharmacotherapy, 20 (3): 369.*
Samir K Mistry et al, "Patient Nonadherence: The $100 Billion Problem," Jul. 1999, American Druggist, pp. 56–63.*
Robert McCarthy, "The price you pay for the drug not taken," Oct. 1998, Business & Health, vol. 16, No. 10, pp. 27–33.*

* cited by examiner

*Primary Examiner*—John Cabeca
*Assistant Examiner*—X. L. Bautista

(57) ABSTRACT

The present invention provides a medical device, or medical navigator, based not on a programming perspective, but a use perspective. Medication to be taken is displayed on a color screen, actual size where possible. A color display is used because the pharmaceutical industry worldwide has substantially standardized on the colors; e.g., black and yellow pills mean barbiturates. Capsules and caplets are uniquely colored for the medicines. Pharmacists can readily tell what the medication is by looking at it. And, patients identify medications by their color and size. Input mechanisms are provided for indicating compliance with the mediation schedule and the physical condition of the patient.

19 Claims, 5 Drawing Sheets

NO ALCOHOL

NO DAIRY

TAKE BETWEEN MEALS

MEDICAL NAVIGATOR AND SYSTEMS THEREFOR

TECHNICAL FIELD

The present invention relates generally to medicine schedule reminders, and more particularly to devices which provide information on medication requirements to patients.

BACKGROUND OF THE INVENTION

Many people today are taking a complicated course of medications, especially people with chronic diseases and many co-morbidities or many different diseases; e.g., diabetes, heart disease, hypertension, kidney disease, peripheral-vessel disease, vision problems, etc., and combinations of diseases such as hypertension and diabetes together. The most chronic diseases are found in individuals who are elderly and typically taking multiple medications, frequently five or more. Many of these medications are taken multiple times a day, and not all of them are taken together. There may be four pills of one medication to be taken during the day, two for another, six for another, and others that are taken every hour.

How to help these people manage their medications has been a longstanding problem; i.e. when to take them and the right number to take. One of the simplest ways to approach this problem which has been with an alarm clock and a detailed instruction sheet showing how to set the alarm clock for the next medication. Very complicated devices have been developed for reminding people to take their medications or to provide for dispensing their medications. The simplest examples are medications which have been customized in blister packs. If, over the course of the day, a patient has to have ten medication cycles, the medicines are clustered by when they need to be taken. There may be three in one blister pack, one in the next, two in the next, three in the next, etc., and the reminders are set according to when each of the blisters needs to be opened and the medication taken.

Other approaches have included programming embedded computers in pill dispensers. Most of these embedded computers are difficult to program because they may have small compartments for the pills, a display where it is necessary to enter the name of the medication and when it is supposed to be taken, the current time, and other associated data in order to program them. The patients themselves often cannot program these computers because they are just too difficult. And even though there are quite a few of these computers, the only place where they seem to have found much use are as adjuncts to drug trials where the clinicians running the drug trials program the embedded computers to be given to the patients for receiving the experimental medications.

Almost all of these devices rely on the language and the pharmaceutical name of the medication. Unfortunately, most people rely on the color or shape of the medication for identification rather than the name.

Proper consumption of medication is a major challenge that is going to exist worldwide for a considerable time because the mean age of the entire population is shifting. There are a lot of older people moving through the demographics in almost all countries, not just the U.S. and Europe and developed Asia. The situation is getting worse for two reasons: the older the individual, the more diseases; and there are more medications for each of the diseases.

DISCLOSURE OF THE INVENTION

The present invention provides a medical navigator based not on a programming perspective, but a use perspective. It has a color picture of the medication to be taken on the dispenser to be used. A picture is used because the pharmaceutical industry worldwide has standardized on the colors. For example, black and yellow pills mean barbiturates. Capsules and caplets are uniquely colored for the medicines. Pharmacists can readily tell what the pill is by looking at it. There is a good reason for this; this is the way patients look at their medications. The medical navigator provides a color picture of the medication to be taken, and, where the size of the screen, permits, the actual size of the medication. This permits medications and dosages to be readily identified by a patient correctly and quickly at the prescribed time. With additional symbol and image grouping, the instructions are presented visually, easily crossing language barriers and other literacy challenges.

The present invention further provides an indication of the time of day a medication needs to be taken. Sunrise would show the sun coming up with a rooster. Mealtime would show the medication superimposed on a plate with food. 'No dairy products' would show a cheese wheel or some representation of a dairy product within a circle with slash of the international "no" sign superimposed on it. Ideally, the medical navigator would be independent of language.

The present invention further provides a simple audio or vibrator reminder so it suits the environment a patient is in. If the patient happens to be in the theatre, a library, or some other place that is quiet, the vibrator can be turned on. Ideally, the medical navigator is approximately credit-card-size, so it can fit in a pocket and the vibrator would signal the reminder. In other cases, a patient may want an audible reminder depending on personal preference or where the patient happens to be.

The present invention further provides interaction with the patient to get to the next medication as an indication that the current medication has been taken. The next medication does not appear until further interaction which indicates whether the person is feeling better or worse. That is the most important information about how a patient is doing: i.e., "Are you feeling as you did?", "Are you feeling better than you felt yesterday?", "Are you feeling worse?" This is done continually to track the outcomes from a patient's perspective. This patient provided compliance and outcomes status enables a much more effective approach to medication management including, but not limited to, development of side effects, co-morbidities, other complications and subtending effectiveness for the entire therapeutic regime reaching beyond the medications alone.

The present invention further provides a medical navigator used with a radio frequency-coupled or infrared-coupled interface from a personal computer or some other type of computer. It can be done by way of a medical service, or it can be done at the pharmacy.

The present invention further provides a medical navigator which has access to the pharmaceutical indexes to display the images for the medications. The medical navigator shows different sizes because there are different doses, so the appropriate one for each dose is shown.

The present invention further provides a medical navigator which shows a scaled replica of medications. Most of the pill forms, capsules and caplets, readily show in actual size. Most of the bottled versions, vaporizers, ampoules, large pads, syringes, and other things rely on some scaled representation. Again, there are different color codes that are used, because there are different medications and doses. The pharmaceutical industry is very knowledgeable about the use models. It is known that patients go by size and color, not name, for their medications.

The present invention further provides a medical navigator which shows a simple dosage as well as the common name for the drug and the time of day for it to be dispensed.

The present invention further provides a medical navigator which can be programmed remotely with a small unit in the home that would act like an answering machine and would cradle the medical navigator. A service could query the device, first to obtain all of the compliance data and then to obtain data regarding how the patient has been feeling, i.e., has he/she been feeling better or worse, and how did that track over the whole medication cycle. Then any new information required for the medications would be downloaded.

The above and additional advantages of the present invention will become apparent to those skilled in the art from a reading of the following detailed description when taken in conjunction with the accompanying drawings.

BEST MODE FOR CARRYING OUT THE INVENTION

Figure 1:
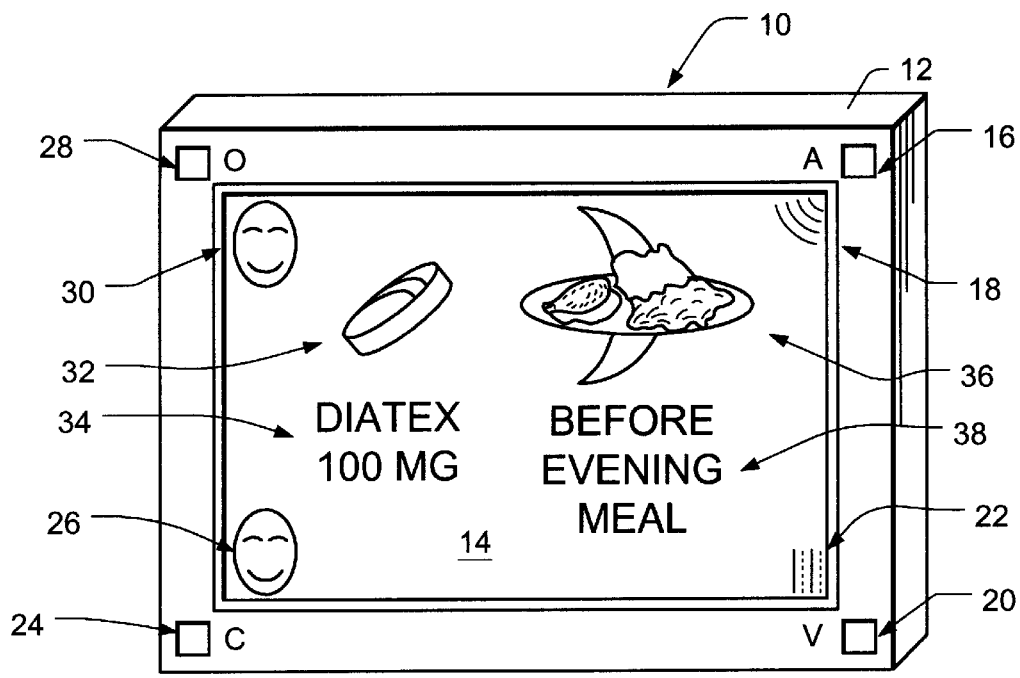
FIG. 1 is an illustration of the medical navigator showing various icons of the present invention.

Referring now to FIG. 1, therein is shown a processor-driven medical navigator 10 which is credit-card-sized and has a frame 12 with a color screen 14. The color screen 14 could be touch-sensitive, but in the best mode there are four buttons, one in each corner of the frame 12. A first button shown in the upper right corner, is an audio (A) alarm button 16. Associated with the audio alarm button 16 is a small audio alarm icon 18 that would let the user indicate whether the audio alarm is active or not active. When it is active, the color screen 14 shows the audio alarm icon 18, which is a simple metaphorical sound wave propagating out of the corner of the color screen 14 adjacent to the audio alarm button 16.

The lower right corner of the medical navigator 10 shows a vibrator (V) alarm button 20 and adjacent to it on the color screen 14 an indicator for whether it is on or off. The color screen 14 shows a vibrator icon 22 of lines and dashes, which is a simple metaphorical representation of vibration, in the screen area immediately adjacent to the vibrator alarm button 20.

The lower left corner of the medical navigator 10 shows a compliance (C) button 24. This is the button the patient would press immediately before or immediately after taking an indicated medication. There is a simple stick-figure face icon called a compliance icon 26 adjacent to the compliance button 24 that shows a happy face when the patient has complied with taking the medication.

The compliance button 24 can also be used to capture non-medication events. With diabetes, for example, compliance with blood sugar testing can be readily captured in conjunction with an image icon for a finger stick.

The upper left corner of the medical navigator 10 shows a patient provided outcome status button, or outcome (O) button 28. The patient presses the outcome button 28 to toggle through responses for how he/she is feeling. The color screen color shows a simple stick-figure face icon, or outcome icon 30. The outcome icon 30 displays an unhappy face for the patient to select if he/she is feeling worse, a face without compassion or expression is shown if feeling the same, and a happy face if feeling better.

The medication that is indicated in FIG. 1 appears as a medication icon 32. In FIG. 1 a tablet is shown in its full size and color. The medication icon 32 shown depends upon the type of medication. Tablets may be shown as an isometric illustration because the thickness is important, especially if it is multicolored. Some tablets have different colors on each side. Capsules may be shown without an isometric illustration.

Immediately under the medication icon 32 is the common trade name 34 for the medication and its dosage, e.g., the name "Diatex" and 100 MG (100 milligrams).

On the right side of the color screen 14 is a timing icon 36, which indicates when the medication should be taken. In this case, the timing icon 36 is a crescent moon behind an illustrated meal on a plate. Because the medication icon 32 is on the left and the timing icon 36 is on the right, the medication is taken before the evening meal. In some cultures these would be placed in the opposite order, for example, where people think in sequence from right to left. Thus, for it to make sense in some parts of the world, the medication icon 32 would need to be shown on the right and the plate of food on the left, in this case. Such an arrangement has been determined to be an effective way of pictorially communicating within the culture for which the medical navigator 10 is to be used. Also, the use of imagery is preferable to language so that even if the medical navigator 10 displays Chinese or Japanese characters, it could be used in the United States by a patient who only reads English because all of the needed information would be available in pictorial form. The written timing icon 38 in this example displays the text 'BEFORE EVENING MEAL' in English.

This permits medications and dosages to be identified by a patient correctly and quickly at the prescribed time, and with additional symbol and image grouping, the instructions are presented visually, easily crossing language barriers.

Figure 2:
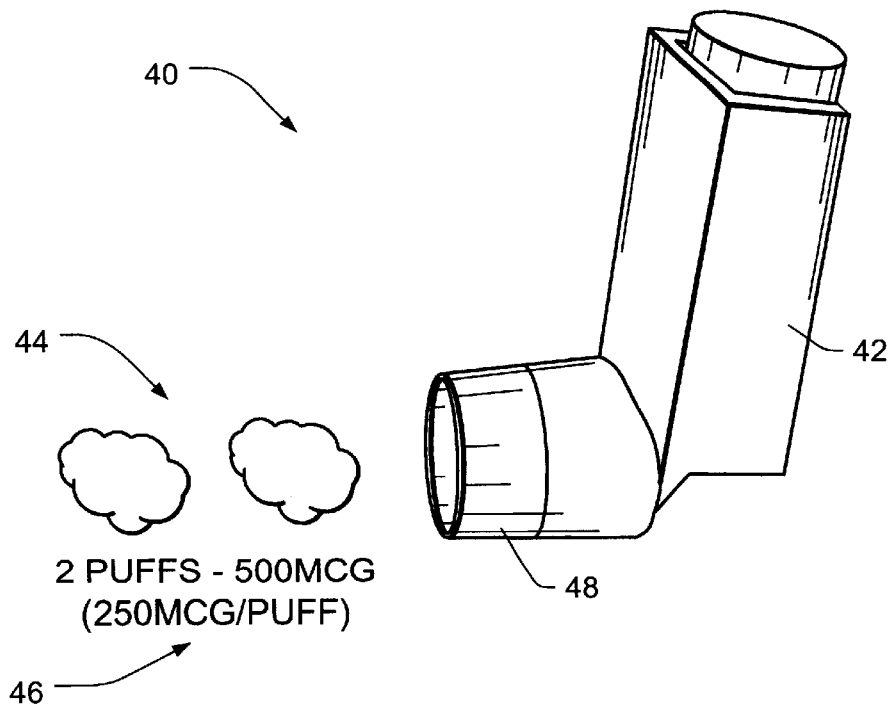
FIG. 2 is a depiction of one icon with instructions of the present invention.

Referring now to FIG. 2, therein is shown an illustration of a different medication icon 40 that would be used. In this case, this is an inhaler icon 42, or vaporizer icon, and it shows that the medication is delivered in two puffs 44. Again, under the inhaler icon 42 would be the written instructions 46 "2 PUFFS–500 MCG, (250 MCG/Puff)". The inhaler icon 42 would substitute for the Diatex in FIG. 1. This illustrates a different medication and the imagery for it that would be placed in the same position as the caplet image and Diatex 100 MG in FIG. 1. All of the medications are color-coded, so the type and amount of medication will be recognized. The inhaler icon 42 would be color-coded also at a nozzle 48 and may have multiple colors. Although optional, manufacturers tend to use common colors for the same medications and dose ranges.

Most of the bottled versions, vaporizers, ampoules, large pads, syringes, and other items rely on some scaled representation. Again, there are different color codes that are used, because there are different medications and doses. The pharmaceutical industry is very knowledgeable about the use models. It is known that patients go by size and color, not name, for their medications.

Figure 3:
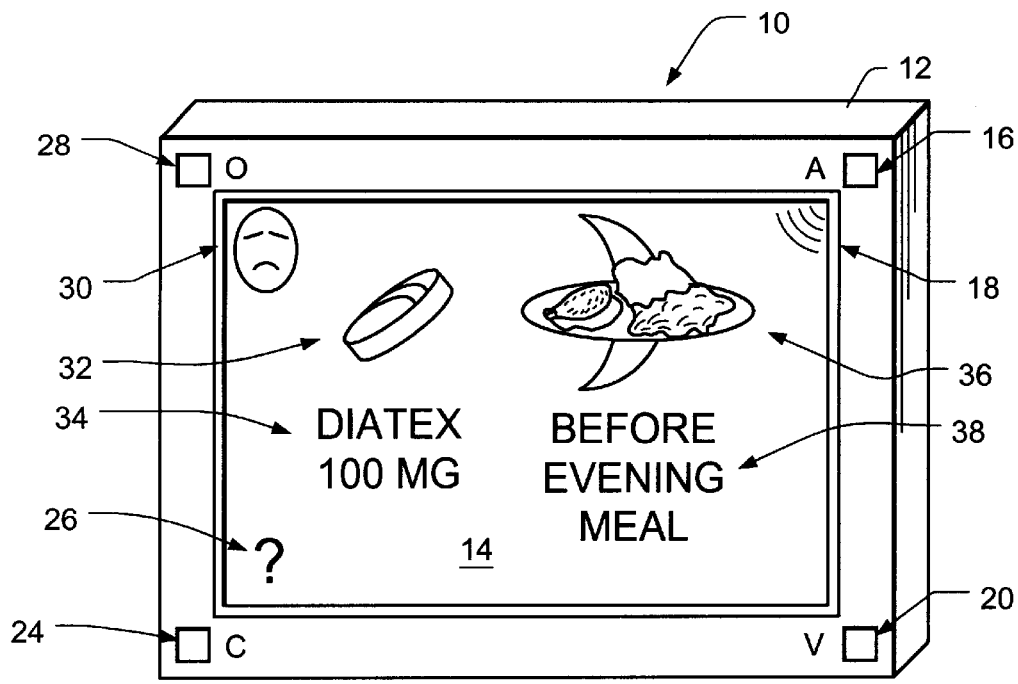
FIG. 3 is an illustration of the medical navigator at one exemplary time of a medication cycle.

Referring now to FIG. 3, therein is shown an illustration of the medical navigator 10 at one exemplary time in a medication cycle. In this case, the compliance icon 26 shows a question mark next to the compliance button 24 because nothing has happened; i.e., time for taking this medication has come and gone. The color screen 14 also shows that the patient has not been doing very well as indicated by the unhappy face toggled to by the patient in the outcome icon 30. In FIG. 3, the audio alarm icon 18 is shown "on" by the sound wave image and the vibrator icon 22 is shown "off" by the lack of the dashed and solid lines. The time that the outcome icon 30 remains on the color screen 14 is the time that gets recorded.

Figure 4:
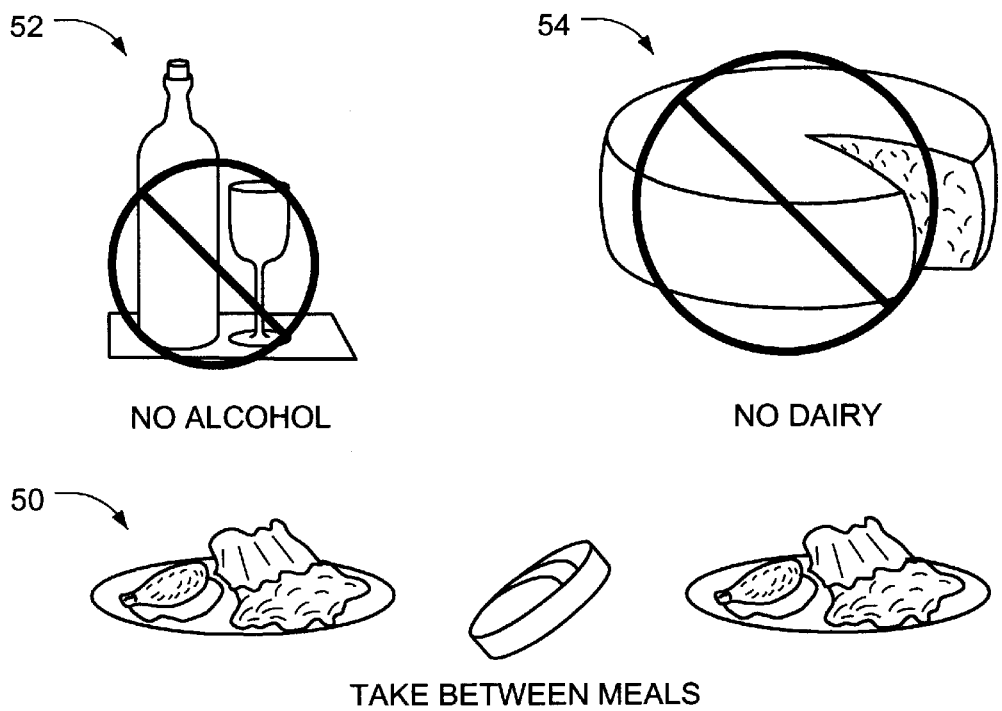
FIG. 4 is a depiction of additional icons of the present invention.

Referring now to FIG. 4, therein is shown a series of instructional icons which are a part of the present invention. A timing icon 50 shows that a caplet is to be taken between meals and notice icons 52 and 54 show that there should be no alcohol or dairy products taken with this medication, as depicted, respectively, by a wine bottle and glass and a cheese wheel with a circle superimposed by diagonal slashes, the international "no" sign. This illustrates the kind of cluster that would show up on the medical navigator 10 for the instructions, purely in pictorial form for how and when to take medication.

Figure 5:
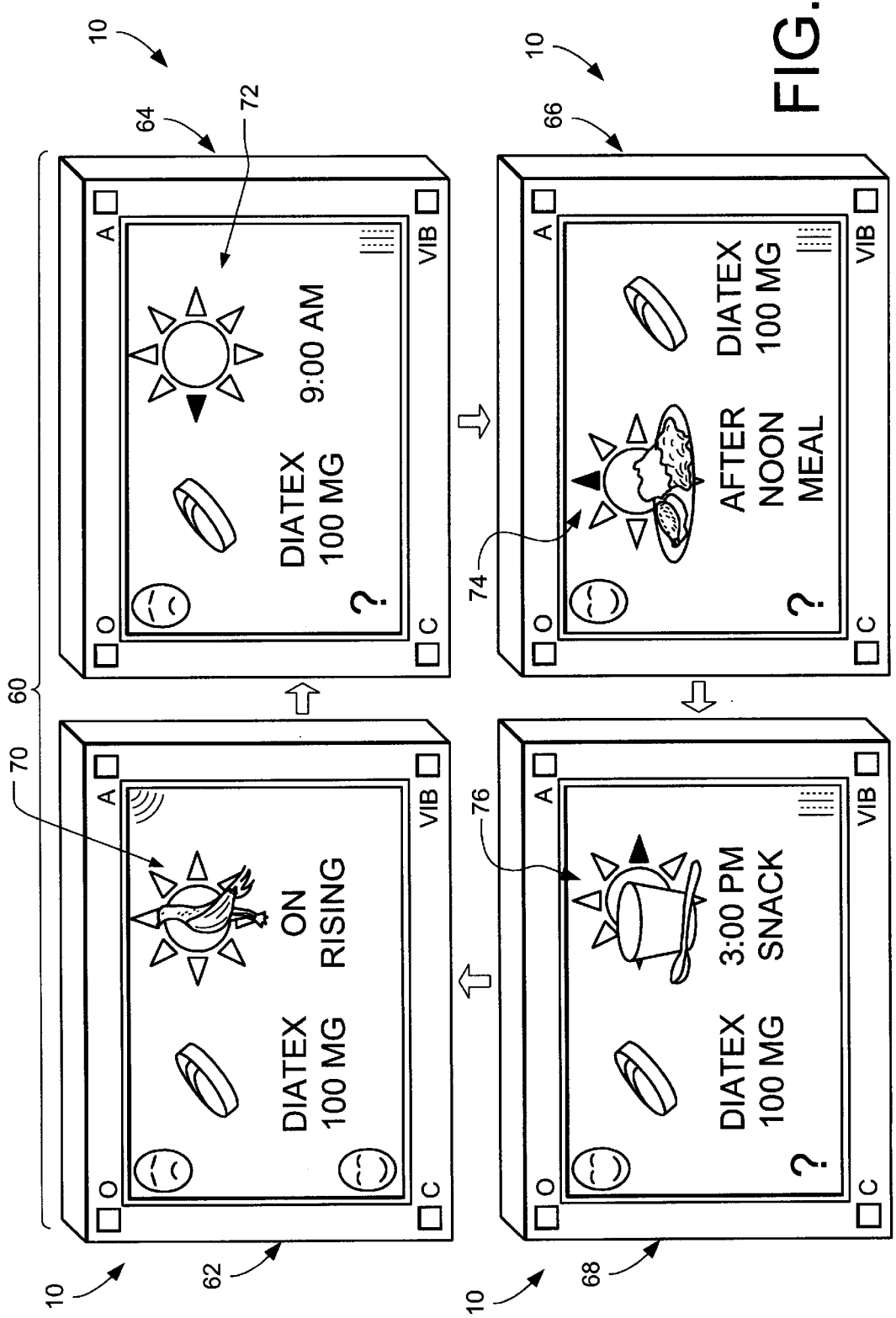
FIG. 5 is an illustration of the medical navigator at four exemplary times of a medication cycle.

Referring now to FIG. 5, therein is shown an exemplary patient medication cycle 60. The medical navigator 10 is shown at four different times by the color screen 14 being shown in four different configurations 62, 64, 66, and 68. The time icons 70, 72, 74, and 76, respectively, show: "at rising" (a stylized sunburst with superimposed rooster); at 9:00 a.m. (a stylized sunburst with a darkened ray at 9:00); after the noon meal (a stylized sunburst with a darkened ray at 12:00 and a superimposed meal followed by the medication icon); and finally at 3:00 p.m. (a stylized sunburst with a darkened ray at 3:00 and a superimposed yogurt cup and spoon). In configuration 62, the patient was not feeling well and took the medication at that time. The configuration 64 shows it is 9:00, the medication has not yet been taken, and the patient is not feeling well. The configuration 66 shows that the patient is feeling better than before and that the medication has not been taken. In this case it shows it after the noon meal. Then configuration 68 shows the patient is feeling fine, has not taken the Diatex yet, but will have to take it with a snack, so it shows a cup of yogurt with a spoon. There are many different combinations possible.

This is done continually to track the outcomes from a patient's perspective. This patient provided compliance and outcomes status enables a much more effective approach to medication management including, but not limited to, development of side effects, co-morbidities, other complications and subtending effectiveness for the entire therapeutic regime reaching beyond the medications alone. The overall operation and use of the medical navigator 10 is shown in this FIG. 5. Many extensions will be evident to those skilled in the art.

Figure 6:
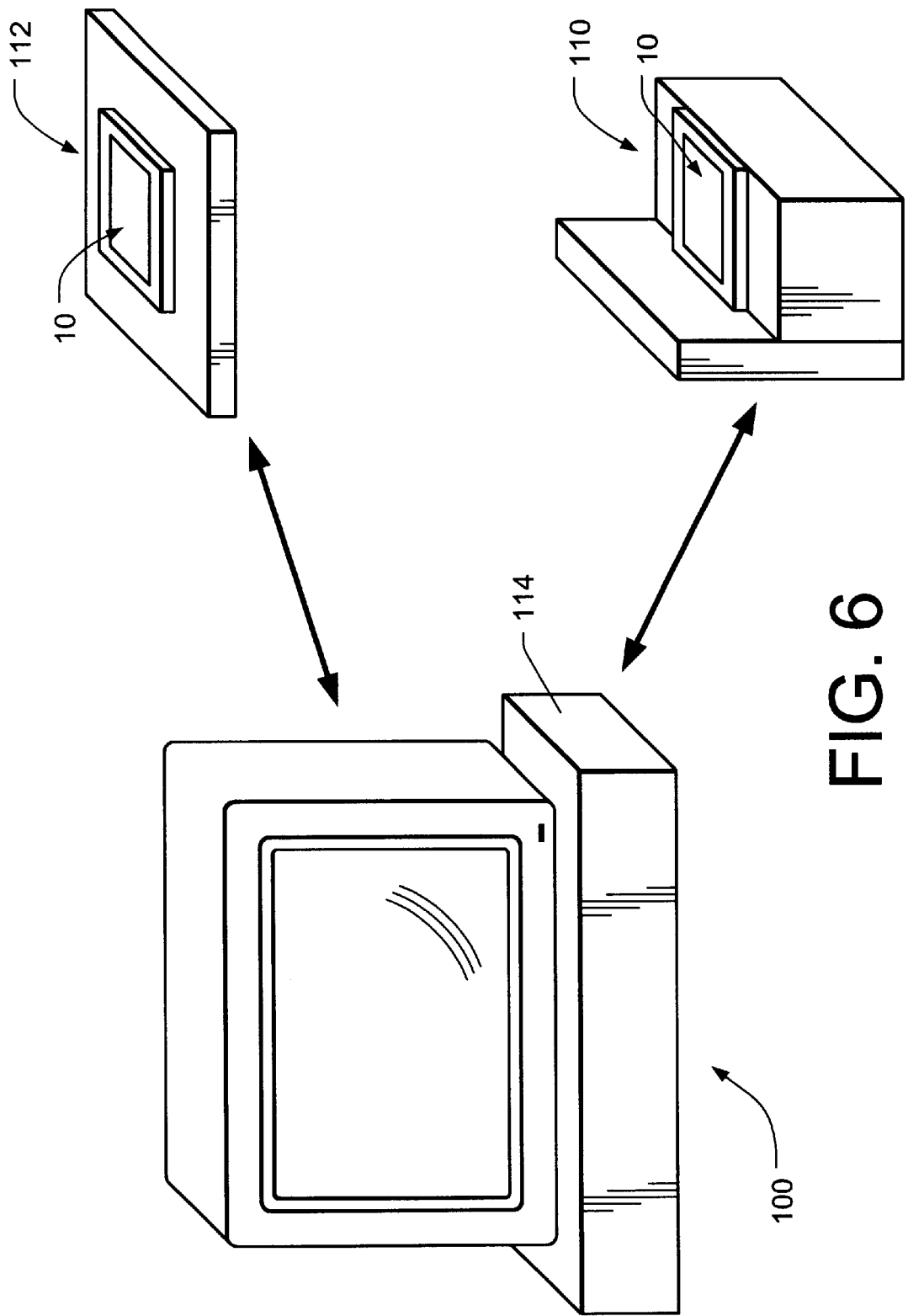
FIG. 6 is a pharmacy system with which the medical navigator is used.

Referring now to FIG. 6, therein is shown a pharmacy system 100 with two code-cache devices 110 and 112. The code-cache device 110 is connected by an infrared (IR) link to a computer 114, and the code-cache device 112 is connected by a radio frequency (RF) link. Similarly, the medical navigator 10 can be connected to the code-cache devices 110 and 112 by the same type of links. The computer 114 downloads the code for the programming and caches it in the code-cache devices 110 and 112 until the medical navigator 10 is dropped in for that patient. The entire pharmacy system 100 gets updated, as well as any data that the pharmacy wants in order to review how the medication regimen has been affecting the care of the patient.

Most of the bottled versions, vaporizers, ampoules, large pads, syringes, and other items rely on some scaled representation. Again, there are different color codes that are used, because there are different medications and doses. The pharmaceutical industry is very knowledgeable about the use models. It is known that patients go by size and color, not name, for their medications.

Figure 7:
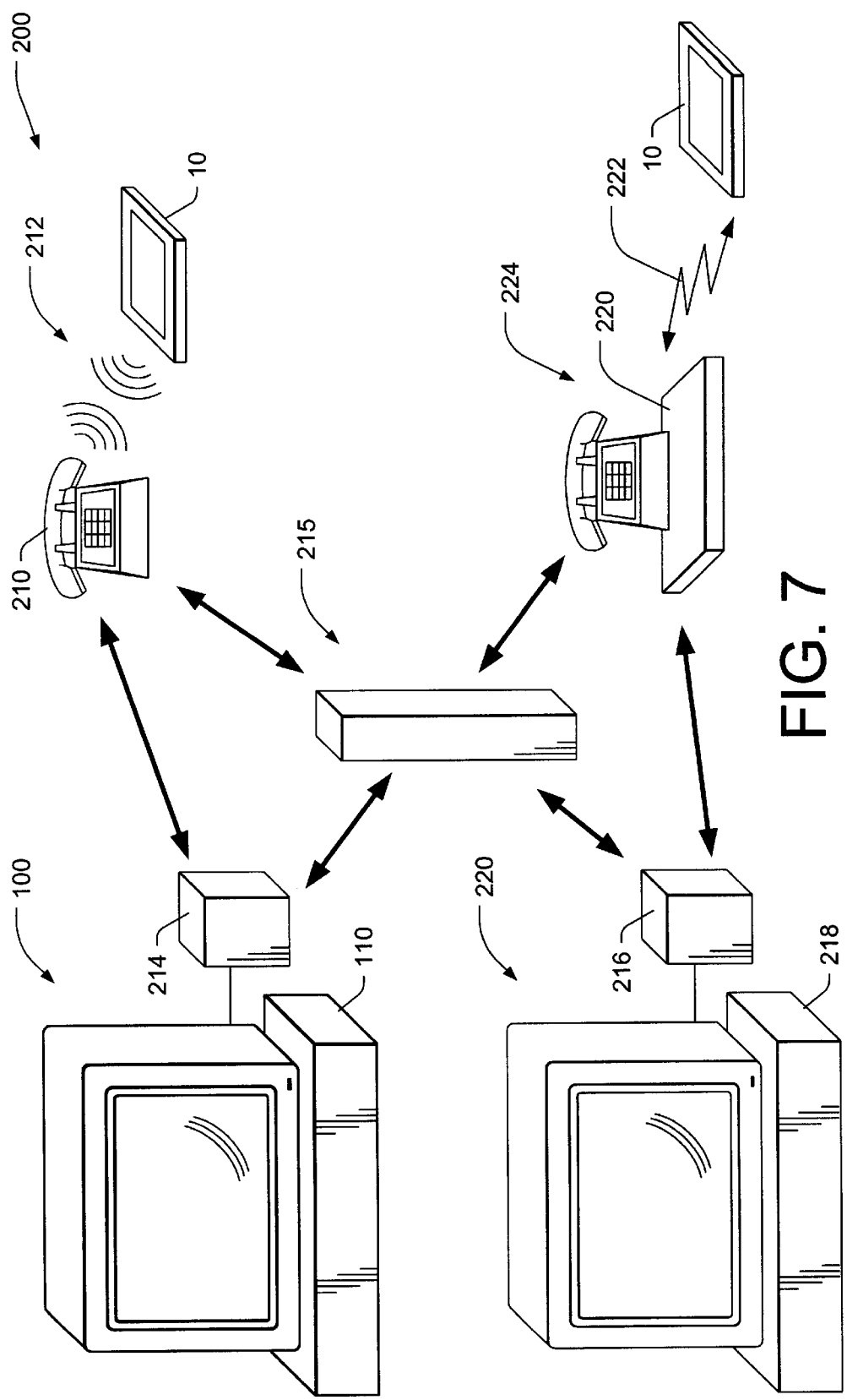
FIG. 7 is an overall medical system with which the medical navigator is used.

Referring now to FIG. 7, therein is shown an overall medical system 200 with which the medical navigators 10 are used. The pharmacy system 100 and its computer 110 are connected to a code-cache device 214 which is directly linked to a plain old telephone system, or "POTS", which is connectable to a patient's telephone 210. By inserting an acoustic coupler in the medical navigator 10, an audio link 212 can be established. The audio link 212 would allow communication of the medical navigator 10 with the code-cache device 214.

The POTS could also be used to connect both the telephone 210 and the code-cache device 214 to a medical database server 215.

The medical database server 215 can also be connected by the POTS to a code-cache 216 of a computer 218 for a clinician/provider system 220. The medical database server 215 further could be connected by the POTS to a network of nodes 224 which could be connectable by IR and RP links 222 to a number of medical navigators 10 for different patients of a clinician or provider.

In operation, the physician would provide various prescriptions for the pharmacist to enter into the pharmacy system 100 which would provide the information to the medical database server 215 and then would be loaded into a medical navigator 10 using the code-cache device 214 as indicated in FIG. 7. The patient would take the medication according to the possible configurations 62, 64, 66, and 68 as shown in FIG. 5.

The patient would use the audio alarm button 16 or the vibrator alarm button 20 to provide audio or physical indications that a medication is to be taken. By looking at the color screen 14, as shown in FIG. 1, and by the arrangement of the medication icon 32 (which could show a number of tablets if more than one were indicated), and the timing icon 36, it would be easy to determine which medication is to be taken. The medication icon 32 could also show notice icons 52 and/or 54 as shown in FIG. 4.

Referring back to FIG. 1, the audio or physical alarm could be stopped by pressing the audio alarm button 16 or the vibrator alarm button 20, as appropriate. The patient would then press the compliance button 24 and make sure that the patient provided compliance icon 26 had switched to a happy face. The patient then could indicate health status by toggling the outcome button 28 until the appropriate outcome icon 30 was reached.

Periodically through the audio link 212, the medical navigator 10 would provide information to the medical database server 215. Information in the medical database server 215 could be accessed by the clinician/provider system 220 when desired and changes to the medication communicated back to the medical navigator 10. Similarly, the medical database server 215 can communicate the same information to the pharmacy system 100 which could provide updates and warnings regarding the medication being taken by the patient.

Whenever the patient needs a new prescription or a refill, the medical navigator 10 could be taken to the pharmacy and inserted in the code-cache devices 110 or 112 as shown in FIG. 6 to be updated.

Many of the medical dispensers rely on some scaled representation. Again, there are different color codes that are used, because there are different medications and doses. The pharmaceutical industry is very knowledgeable about the use models. It is known that patients go by size and color, not name, for their medications.

While the invention has been described in conjunction with a specific best mode, it is to be understood that many alternatives, modifications, and variations will be apparent to those skilled in the art in light of the a foregoing description. Accordingly, it is intended to embrace all such alternatives, modifications, and variations which fall within the spirit and scope of the included claims. All matters set forth herein or shown in the accompanying drawings are to be interpreted in an illustrative and non-limiting sense.

The invention claimed is:

1. A medical device for a patient comprising:
a color screen;
an indication mechanism for prompting the patient to look at said color screen;
an input mechanism; and
a processor connected to said color screen, said indication mechanism, and said input mechanism, said processor causing said indication mechanism to cause said prompting at a predetermined time to indicate when a medication is to be taken, said processor provides a timing icon at the predetermined time on said color screen, said timing icon including a written language display of when the medication is to be taken, said timing icon display the time and a pair of icons positionable on said color screen to indicate by relative position to said medication icon the proper timing to take the medication, said processor causing a medication icon to appear on said color screen at the predetermined time, said medication icon showing a color image of a medication to be taken by the patient, and said processor responsive to said input mechanism to reset the predetermined time.

2. The medical device as claimed in 1, including:
a compliance input mechanism for input of information that the patient has taken a medication.

3. The medical device as claimed in claim 2 wherein:
said processor is responsive to said compliance input mechanism to provide a compliance icon in response to input therefrom indicative of the patient having taken a medication.

4. The medical device as claimed in claim 1 including:
an outcome input mechanism for the input of patient physical condition information.

5. The medical device as claimed in claim 4 wherein:
said processor is responsive to said outcome input mechanism to provide an outcome icon on said color screen.

6. The medical device as claimed in claim 1 wherein:
said timing icon displays the time.

7. The medical device as claimed in claim 1 wherein:
said processor causing said medication icon to appear on said color screen further causes a medical cautionary icon to appear.

8. The medical device as claimed in claim 1 including:
a pharmacy system; and
a link to said pharmacy system for communication with said processor regarding the medication for the patient.

9. The medical device as claimed in claim 1 including:
a clinician/provider system; and
a link for communication with said processor regarding the physical condition of the patient.

10. The medical device as claimed in claim 1 including:
a medical system including a pharmacy system and a clinician/provider system; and
a linking system for communication of patient medical and physical information among said processor, said pharmacy system, and said clinician/provider system.

11. A medical device for a patient comprising:
a color screen;
an indication mechanism for prompting the patient to look at said color screen, said indication mechanism selectable to provide an indication selected from a group consisting of an audio, a physical, and a combination indication;
an input mechanism; and
a processor connected to said color screen, said indication mechanism, and said input mechanism, said processor causing said indication mechanism to cause said prompting at a predetermined time, said processor causing a medication icon to appear on said color screen at the predetermined time to indicate when a medication is to be taken, said process provides a timing icon at the predetermined time on said color screen, said timing icon including a written language display of when the medication is to be taken, said timing icon displays the time and a pair of icons positionable on said color screen to indicate by relative position to said medication icon the proper timing to take the medication, said processor capable of causing an actual-size medication icon to be displayed, said medication icon showing a color image of a medication to be taken by the patient, and said processor responsive to said input mechanism to reset the predetermined time.

12. The medical device as claimed in 11, including:
a compliance input mechanism for input of information that the patient has taken a medication in accordance with said medication icon.

13. The medical device as claimed in claim 12 wherein:
said processor is responsive to aid compliance input mechanism to provide a compliance icon in response to input therefrom and to reset the predetermined time.

14. The medical device as claimed in claim 11 wherein:
an outcome input mechanism for the patient to input physical condition information, said outcome input mechanism capable of receiving a plurality of possible inputs.

15. The medical device as claimed in claim 14 wherein:
said processor is responsive to said outcome input mechanism to provide a plurality of different outcome icons on said color screen, said outcome icons including icons indicating if the patient feels better, worse, or the same.

16. The medical device as claimed in claim 11 wherein:
said processor causing a medication icon to appear on said color screen causes a medical cautionary icon to appear indicating no alcohol, do not drive, no dairy products, or a combination thereof.

17. The medical device as claimed in claim 11 including:
a pharmacy system; and
a link to said pharmacy system for communication with said processor for updating the medication and medication information for the patient, said link including a wireless link.

18. The medical device as claimed in claim 11 including:
a clinician/provider system; and
a link for communication with said processor regarding the physical condition of and medication instructions for the patient, said link including a wireless link.

19. The medical device as claimed in claim 11 including:
a medical system including a pharmacy system and a clinician/provider system; and
a linking system for communication of patient medical and physical information among said processor, said pharmacy system, and said clinician/provider system, said linking system including a wireless link and a telephone link.

* * * * *